US00PP17310P3

(12) United States Plant Patent

Hockenberry Meyer

(10) Patent No.: US PP17,310 P3
(45) Date of Patent: Dec. 26, 2006

(54) *SCHIZACHYRIUM* PLANT NAMED 'MINNBLUEA'

(50) Latin Name: *Schizachyrium scoparium*
Varietal Denomination: MinnblueA

(75) Inventor: Mary Hockenberry Meyer, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 19 days.

(21) Appl. No.: 11/104,685

(22) Filed: Apr. 13, 2005

(65) Prior Publication Data

US 2005/0235390 P1 Oct. 20, 2005

Related U.S. Application Data

(60) Provisional application No. 60/563,040, filed on Apr. 16, 2004.

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Schizachyrium scoparium*, 'MinnblueA', that is characterized by its tall, narrow, upright form that does not lodge and its unique foliage color that is blue with highlights of burgundy in summer changing to a bright mixture of colors in fall including tones of purple, blue, red, pink, burgundy, and orange. 'MinnblueA' is further characterized by its ability to grow in a wide range of soil types including heavy clay, dry, and alkaline soils.

2 Drawing Sheets

Botanical classification: *Schizachyrium scoparium.*
Varietal denomination: 'MinnblueA'.

BACKGROUND OF THE INVENTION

The present invention relates to a new and distinct cultivar of *Schizachyrium scoparium* and will be referred to hereafter by its cultivar name, 'MinnblueA'. 'MinnblueA' represents a new cultivar of little bluestem, an ornamental grass grown for landscape use.

The inventor discovered and selected the new cultivar, 'MinnblueA', in a cultivated field in St. Paul, Minn., in the summer of 1996. 'MinnblueA' was discovered as a naturally occurring variant seedling in a cultivated field sown for field evaluations of little bluestem. The field from which 'MinnblueA' was selected was sown with seed collected in the fall of 1995 from a field of open pollinated, unnamed plants of *Schizachyrium scoparium* grown for seed production in Benton County, near Princeton, Minn. The seed collected from the unnamed plants of *Schizachyrium scoparium* was bulked from several individuals, grown in the greenhouse and then plants were transplanted into the cultivated field in St. Paul. It is not possible to identify the parents for 'MinnblueA'.

The new cultivar 'MinnblueA' is unique in several characteristics, which makes this new invention unlike any other known cultivars or varieties of *Schizachyrium scoparium* known to the inventor. 'MinnblueA' has a taller, more upright form than is typical of little bluestem. 'MinnblueA' has dark blue to burgundy foliage during the summer, turning red to purple and violet in the fall. The summer and fall color is unique on a plant that has a tall columnar stature.

Asexual reproduction of the new cultivar was first accomplished by root division in St. Paul, Minn. in 1999 by the inventor. The vegetative propagules of this cultivar have been determined to be stable and are reproduced true to type in successive generations.

SUMMARY OF THE INVENTION

The following traits have been repeatedly observed and represent the characteristics of the new cultivar. 'MinnblueA' has not been observed under all possible environmental conditions. The phenotype may vary somewhat with variations in temperature, day length, light intensity, soil types and water and fertility levels, without, however, any variance in the genotype. The measurements, observations and descriptions that follow describe plants grown outdoors and observed for six years in St. Paul, Chaska, Morris, Crookston and Plymouth, Minn. These attributes in combination distinguish 'MinnblueA' from any known selections of *Schizachyrium scoparium* known to the inventor.

1. The plant growth habit of 'MinnblueA' is upright and narrow to upright open. The habit of the species is much looser and open, with arching and lodging typical.
2. The height of 'MinnblueA' is 120–140 cm, which is taller than most little bluestem, especially little bluestem in the upper Midwest. The species is typically 20–100 cm, although in southern US, plants can be taller, to 150 cm.
3. Summer color of 'MinnblueA' foliage is medium to light blue, with highlights of dark red and purple. The flowering culms are dark burgundy red. The species color is much more variable from green, to blue green and olive green with similar flowering culm color.

4. Fall color of 'MinnblueA' foliage is much brighter than the species, with light purple, red and pink colors including light blue, burgundy and orange. The fall foliage is often a rainbow of colors. The species tends to be more uniform in color with fewer colors represented.
5. 'MinnblueA' is tolerant of a wide variety of soils and has been grown on heavy clay soils as well as dry sites, which is typical of little bluestem. 'MinnblueA' is tolerant of high pH or alkaline soils and drought once established.

BRIEF DESCRIPTION OF THE DRAWINGS

The accompanying photographs were taken in Chaska and Plymouth, Minn. and illustrate the characteristics of the new cultivar 'MinnblueA'.

The photograph in FIG. 1 depicts the plant habit and foliage coloration of 'MinnblueA' as observed in November.

Figure 1:
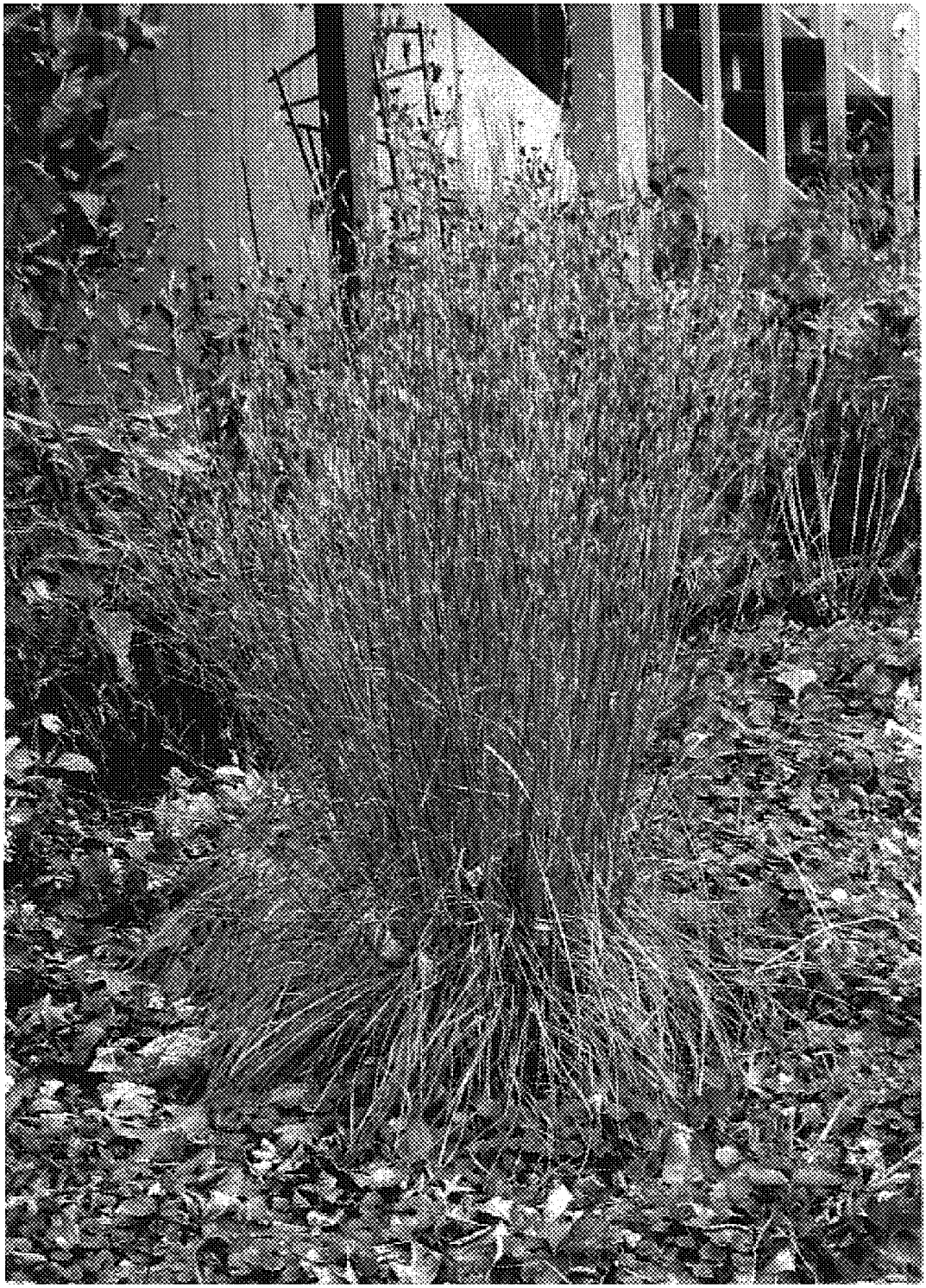
Figure 2:
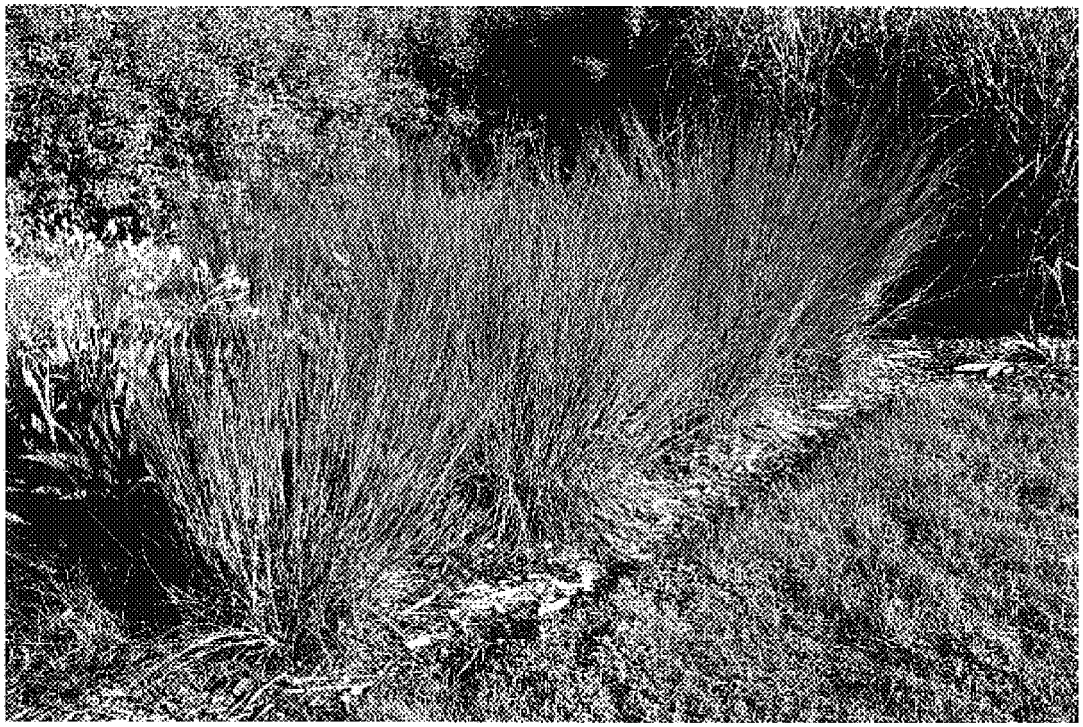

The photograph in FIG. 2 depicts four plants of 'MinnblueA' grown side-by side and illustrates the foliage color in September and the consistency of characteristics of 'MinnblueA'.

The colors in the photographs are as close as possible with the photographic and printing technology utilized. The color values cited in the detailed botanical description accurately describe the colors of the new little bluestem.

DETAILED BOTANICAL DESCRIPTION

The following is a detailed description of the new cultivar as grown in five outdoor field settings for six years from a single plant from the cultivated field in St. Paul, Minn. The color names and numbers refer to the 1995 Royal Horticultural Society's Colour Chart, London, England; except for general color terms of ordinary dictionary significance are used.

Botanical classification: 'MinnblueA' is a cultivar of *Schizachyrium scoparium.*

Common name: 'MinnblueA' little bluestem.

Parentage: 'MinnblueA' is a naturally occurring variant seedling grown from seed collected from open pollinated parents that were growing in a field of unnamed plants of *Schizachyrium scoparium.*

General description:

*Blooming period.*—September and October, with seed forming in October.

*Plant habit.*—Herbaceous perennial grass, upright and narrow, thick fine textured foliage, long-lived.

*Height and width or spread.*—100–138 cm height in bloom, 60–85 cm in width. Moderate vigor.

*Hardiness zone.*—USDA Zones 3–9.

*Culture.*—Grows well in full sun, in most soils. Tolerant of drought and alkaline soils.

*Diseases and pests.*—*Schizachyrium scoparium* is relatively free of disease. No susceptibility of resistance to disease or pests has been observed for 'MinnblueA'.

*Root description.*—Fibrous, wiry, light brown numerous roots, 30–90 cm in length, up to 1 cm in diameter, plants are deep rooted.

Growth and propagation:

*Propagation.*—Root division, probably basal stem cuttings and tissue culture.

*Growth.*—Plants develop into a one-gallon container plant in 10–12 weeks when grown in a greenhouse with ambient lighting and an average temperature of 68 degrees F.

Culm (stem) description:

*General.*—Cylindrical, solid, thin but strong, erect, upper half freely branching, sheaths often grayish villous.

*Culm color.*—Red-purple 59A; to violet 85A; to violet blue 92A and 92B.

*Culm size.*—2–4 mm in diameter, averaging 140 cm in height from the base to the tip of the flower panicle.

*Stem surface.*—Glabrous.

*Internode length.*—16 to 19 cm at the base, decreasing to 15–13 mid-culm, reduced to 6–9 cm near the summit.

Foliage description:

*Leaf shape.*—Linear, sparsely pilose at their junction, flat.

*Leaf division.*—Simple, margins entire.

*Leaf base.*—Sheathed to base of the culm.

*Leaf venation.*—Parallel, foliage color can vary from top to bottom.

*Leaf width.*—3–6 mm wide, average of 4 mm.

*Leaf length.*—Basal leaves 53–60 cm, mid-culm foliage 30–40 cm. near the apex of the culm 10–20 cm.

*Leaves per culm.*—Typically 4–7.

*Leaf surface.*—Glabrous.

*Leaf collar type.*—Continuous.

*Leaf arrangement.*—Alternate, 2 ranked.

*Leaf auricle.*—Not present.

*Leaf persistance.*—Foliage dries but persistent through winter.

*Leaf attachment.*—Sheathed.

*Ligule.*—1 mm in width, membranous.

*Leaf color* (*upper and lower surface*).—Summer: blue-green 122C and 122D to greyed green 189 B and 189C with tips of greyed purple, 187 A and 187B. Fall: greyed colors of orange 171 A and 171B; to red 180A, 182A and 182B; to purple 184B, 184C, 185C and 186C.

Flower description: Flowers are as typical of *Schizachyrium scoparium*, with multiple, typically 3–5, racemes present per flowering culm. Racemes are 10–15 cm in length and red-purple 59A; to violet 85A; to violet blue 92A and 92B in color. Spikelets are sparse along racemes and arranged in pairs at each node of an articulate rachis, one sessile and perfect, the other pedicellate and either staminate, neuter, or reduced to a pedicle. Spikelets appressed to the rachis, the sessile spikelet falling attached to a pedicle and a section of the rachis. Sessile spikelet 6–8 mm long, fertile, 8–15 mm awned, the pediceled spikelet reduced but usually present, short awned. Glumes of the sessile spikelet large and firm. Lemmas of the sterile and fertile florets thin and membranous. Rachis and pedicels of the sterile spikelet often villous, sometimes conspicuously so. Peduncle is an average of 1.5 mm in diameter, ranges from 0 to 8 cm in length and color is red-purple 59A; to violet 85A; to violet blue 92A and 92B. Reproductive organs are very small, fleeting or scarce in presence and therefore difficult to describe. The lastingness of the inflorescence is about two weeks.

Caryopsis: Lemma and palea adhering to the caryopsis, actual caryopsis very small and fine, less than 1 mm.

I claim:

1. A new and distinct cultivar of *Schizachyrium* plant named 'MinnblueA' as herein illustrated and described.

* * * * *